United States Patent
Lee et al.

(10) Patent No.: US 9,291,611 B2
(45) Date of Patent: Mar. 22, 2016

(54) METHODS FOR QUANTITATIVE ANALYSIS OF ASBESTOS IN VERMICULITE-CONTAINING MATERIALS

(71) Applicant: RJ LEE GROUP, INC., Monroeville, PA (US)

(72) Inventors: Richard J. Lee, Murrysville, PA (US); Matthew Spencer Sanchez, Murrysville, PA (US); Alan M. Levine, Monroeville, PA (US)

(73) Assignee: RJ LEE GROUP, INC., Monroeville, PA (US)

(*) Notice: Subject to any disclaimer, the term of this patent is extended or adjusted under 35 U.S.C. 154(b) by 442 days.

(21) Appl. No.: 13/918,071

(22) Filed: Jun. 14, 2013

(65) Prior Publication Data

US 2014/0370610 A1     Dec. 18, 2014

(51) Int. Cl.
*G01N 33/38* (2006.01)
*G01N 1/34* (2006.01)

(52) U.S. Cl.
CPC . *G01N 33/38* (2013.01); *G01N 1/34* (2013.01)

(58) Field of Classification Search
CPC ......... G01N 33/38; G01N 1/34; G01N 31/22; G01N 23/223
See application file for complete search history.

(56) References Cited

U.S. PATENT DOCUMENTS 3,458,393 A * 7/1969 Battista .................. C01B 33/22
                                                      106/287.34
5,004,920 A    4/1991 Lee et al.

OTHER PUBLICATIONS

Method for the Determination of Asbestos in Bulk Building Materials R.L. Perkins and B.W. Harvey EPA/600/R-93/116 Jul. 1993.*
Environmental Laboratory Approval Program Certification Manual, Item 198.4 Nov. 22, 2006.*
Model AHERA Asbestos Management Plan for Local Education Agencies Mar. 2004.*
Asbestos NESHAP Regulations for Renovation and Demolition Activities Jun. 26, 2012.*
Environmental Protection Agency, Asbestos Hazard Emergency Response Act (AHERA); Fed. Reg. 52, (210), 41845, 41846, 1987.
Environmental Protection Agency, National Emission Standards for Hazardous Air Pollutants (NESHAP) Fed. Reg. 55 (224), 48405, 48415, 1990.
Environmental Protection Agency, Method for the Determination of Asbestos in Bulk Building Materials, Jul. 1993.

(Continued)

*Primary Examiner* — Krishnan S Menon
*Assistant Examiner* — Dwan A Gerido
(74) *Attorney, Agent, or Firm* — Eckert Seamans Cherin & Mellott, LLC; Arnold B. Silverman

(57) ABSTRACT

A method for quantitative analysis of asbestos in vermiculite-containing materials includes a first embodiment which includes washing the sample with water or treating the sample with a low concentration acid to digest gypsum and carbonates, ashing the sample at a low temperature to remove cellulose, therefrom and analyzing the sample. Digestion may be effected before or after ashing. Subsequently, a second subsample may be ashed at low temperature to remove cellulose and refluxed with a concentrated acid followed by refluxing with a base and rinsing with deionized water to wash away gypsum, vermiculite and other soluble components. This is followed by analysis to determine asbestos concentration. In a further embodiment, the residue of the first embodiment may be employed as the second subsample.

22 Claims, 2 Drawing Sheets

(56) References Cited

OTHER PUBLICATIONS

Environmental Protection Agency, Research Method for Sampling and Analysis of Fibrous Amphibole in Vermiculite Attic Insulation, Jan. 2004.

Matthew S. Sanchez and Mickey E. Gunter, Quantification of amphibole content in expanded vermiculite products from Libby, Montana U.S.A. using powder X-ray diffraction, vol. 91, American Mineralogist, 2006, pp. 1448-1451.

Mickey E. Gunter and Matthew S. Sanchez, Amphibole content of commercial vermiculites by powder X-ray diffraction, International Journal of Mineralogy, Crystallography, Geochemistry, Ore Deposits, Petrology, Volcanology, 2008, 77, 2, 35-41.

Environmental Laboratory Approval Program Certification Manual, Transmission Electron Microscope Method for Identifying and Quantitating Asbestos in Non-Friable Organically Bound Bulk Samples, Jan. 2, 2009, item 198.4.

New York State Department of Health, Additional Vermiculite Guidance, (Jun. 22, 2012) (Letter).

* cited by examiner

METHODS FOR QUANTITATIVE ANALYSIS OF ASBESTOS IN VERMICULITE-CONTAINING MATERIALS

BACKGROUND OF THE INVENTION

1. Field of the Invention

The present invention relates to methods for quantitatively analyzing asbestos in vermiculite-containing materials, and more specifically, involves water such as a deionized water or a weak acid. The acids may include mineral acids or organic acids. Such acids preferably include acids selected from the group consisting of HCl, HBr, $HCrO_4$, $H_2SO_4$, and $HNO_3$, and organic acids including citric acid, acetic acid, and formic acid. The wash and a low temperature ash process with efficient elimination of certain constituents of the vermiculite-containing materials that would otherwise obscure detection, to permit the material to be concentrated, and permit accurate determination of asbestos content. In other embodiments, after the ash process, the specimen is subjected to a concentrated acid reflux followed by a high base reflux

2. Description of the Prior Art

It has long been known that exposure to asbestos creates a high risk of cancer in those exposed. As a result of an enormous amount of older buildings having employed asbestos-containing materials prior to awareness of this cancer risk, a serious problem exists with respect to determining if vermiculite-containing insulation and fireproofing materials contain asbestos at such a level as to present a health risk. Asbestos present in such building materials may pose a risk to not only those who are regularly present in the environment, but also those engaged in remediation to remove potentially hazardous asbestos containing vermiculite-containing materials. In addition, disposal of asbestos-containing material (ACM) is regulated and imposes significant disposal costs.

In the interest of health considerations, as well as economic considerations, it is important to determine (a) which vermiculite-containing materials contain a level of asbestos such that the material should be removed from the building or the building demolished and (b) the processes by which it is removed and disposed of.

New York State has issued guidelines regarding vermiculite-containing materials. The guidelines are currently present at <http://www.wadsworth.org/labcert/elapcert/forms/Vermiculite%20Guidance_Rev08 2712.pdf>. New York, in this guideline, has stated that building materials with more than 10% vermiculite will be presumed to be asbestos containing materials ("ACM") and must comply with certain notification and work practices. It further stated that there is a non-rebuttable presumption that there are no reliable sampling protocols for determining asbestos content in vermiculite.

Various means for preparing samples for analysis by various types of apparatus have been known.

U.S. Pat. No. 5,004,920 discloses a method of preparing membrane filters for viewing particles or fibers captured on the filters using transmission electron microscopy. This patent discloses the mounting of a section of the membrane filter on a glass slide with retention being effected by a liquid which will not release the filter when the slide is immersed in a solvent. The filter section is then coated with carbon to replicate the surface of the membrane filter and the particles and fibers thereon. The slide is then immersed in a selected solvent which attacks the filter material and causes the carbon film squares to float off of the membrane filter.

Prior art teachings regarding quantifying asbestos in a specimen of vermiculite-containing materials do not provide the level of sensitivity or precision to meet current requirements. Among other things, the prior art tends to fail to identify and quantify chrysotile, amosite, crocidolite, tremolite, actinolite, and anthophyllite, and other amphibole asbstiforms.

The Environmental Laboratory Approval Program Certification Manual under the subject "Transmission Electron Microscope Method for Identifying and Quantitating Asbestos in Non-Friable Organically Bound Bulk Samples" dated Nov. 22, 2006 item 198.4 discloses the use of ashing to eliminate organic materials followed by a concentrated hydrochloric acid wash infiltration. The high acid levels in this procedure would also preclude it from being employed in current protocols. See also item no. 198.6.

The United States EPA published an outline of a float process to separate vermiculite from mineral fibers which sink. Research Method for Sampling and Analysis of Fibrous Amphibole in Vermiculite Attic Insulation; Method 600/R-04/004; January 2004.

It is also been suggested to use a fluidized bed asbestos segregator which is a sample preparation instrument that utilizes air elutriation to separate asbestos from heavier matrix particles deposited these onto a filter which can then be analyzed by transmission electron microscopy or other microscopic techniques.

Despite the foregoing teachings, there remains a very real and substantial problem in connection with obtaining quantitative analysis of asbestos in vermiculite containing materials in accordance with current standards.

SUMMARY OF THE INVENTION

The present invention has met the above described needs. In one embodiment (FIG. 1), the method of quantitative analysis of asbestos in vermiculite-containing materials includes providing a sample of the vermiculite-containing material, placing the vermiculite-containing material in filtering apparatus and treating the sample with water, such as deionized water or a weak acid solution selected from the group consisting of HCl, HBr, $HCrO_4$, $H_2SO_4$, $HNO_3$, citric acid, acetic acid, or formic acid at a concentration of about 0.1 N to 1.5 N, preferably about 0.1 to 1.2 N, subsequently washing the sample with water, drying it, and measuring weight loss of the sample. The residue is then ashed, preferably at about 450° C. to 550° C., for one to three hours preferably at least two hours. The specimen is then cooled and the ash weight loss is determined. The residue is transferred to a filter employing water and then dried. The percentage weight loss is calculated followed by analyzing the sample to determine the quantity of asbestos in the vermiculite-containing material, whereby cellulose, gypsum and carbonates are removed from the sample.

In another embodiment of the invention after the first test described hereinbefore is performed, there is additional testing of a subsample of the original material to provide further data. The second test may be employed in one embodiment on the residue of the first test as will be disclosed hereinafter with respect to FIG. 2 or, in the alternative, may be performed separately on another portion of the sample which has not been subjected to the first test. If the second test is performed on the ashed residue 26 of the first test, the ashing will preferably have been performed at about 450° C. to 550° C., for one to three hours preferably at least two hours and calculation of the sample percent weight loss. The ashed residue is refluxed in an acid selected from the group consisting of HCl HBr, $HCrO_4$, $H_2SO_4$, $HNO_3$, citric acid, acetic acid, and formic acid in a concentration of about 8 N to 12 N (preferably 12 N) at room temperature, the sample is filtered, water washed and filtered. It is then refluxed with a high base, preferable, such as NaOH or KOH, at about 200° C. to 400° C. and preferably about 325° C. to 375° C., preferably 4 N for about 2 hours to 4 hours. This separates gypsum, vermiculite and other soluble components from the sample. After the sample has been cooled, it is diluted with water and filtered, the sample is dried, weighed and then analyzed.

Analysis can be advantageously performed in respect of the first segment of the method employing polarized light microscopy. Analysis can be obtained in the second portion by employing one or more methods selected from the group consisting of polarized light microscopy, transmission electron microscopy, scanning electron microscopy, and X-ray diffraction.

In the alternate embodiment, the first test will be performed on a first portion of the sample and the second test will be performed on a second portion of the sample. When this embodiment is employed, a cone quartering or riffle splitting technique is employed to collect a representative subsample weighing about 0.1 g to 1.0 g. This subsample is then weighed and ashed in a muffle furnace starting at room temperature and then heated for a minimum of about 2 hours at about 450° C. to 550° C. and preferably about 460° C. to 500° C. The sample is then cooled and ash weight loss is determined. The residue is transferred onto a filter using deionized or distilled water and then the residue is dried at about 60° C. The percentage weight loss is then determined by weighing. Next, the preweight ash sample is introduced into a suitable vessel and refluxed at about 100 mL of concentrated acid such as an acid selected from the group consisting of HCl, HBr, $HCrO_4$, $H_2SO_4$, $HNO_3$, citric acid, acetic acid and formic acid at about 250° C. for one hour. The samples are allowed to cool and then are filtered through a suitable filter. The sample is then rinsed thoroughly and filtered. The particulate is transferred back to a suitable vessel and refluxed with a high base, preferable 4M of NaOH or KOH, at about 200° C. to 400° C. and preferably about 325° C. to 375° C. for about 2 to 4 hours. The samples are allowed to cool and are diluted with deionized water and filtered onto a suitable filter which may be a 0.2 µm polycarbonate filter. The samples are then dried and desiccated. The sample may then be split onto different filters and analyzed by at least one means selected from the group consisting of polarized light microscopy, transmission electron microscopy, scanning electron microscopy and X-ray diffraction to determine the amount of asbestos in the sample.

It is an object of the present invention to provide effective methods for quantitatively determining the amount of asbestos in a vermiculite-containing material.

It is a further object of the present invention to provide a method which will effectively and accurately make a quantitative determination of the amount of asbestos in a vermiculite-containing material with a first phase of the method, processing the same in a weak acid solution followed by ashing at a relatively low temperature.

It is a further object of the present invention to effectively remove from vermiculite-containing materials certain non-asbestos materials in order to permit more precise measurement of the quantity of asbestos present in the material.

It is a further object of the invention to optionally use of a second phase of the method, depending upon analysis objectives, by employing the original material after ashing, refluxing in a concentrated acid, cooling, filtering, rinsing and filtering with the particulate material then being refluxed with a strong base, such as NaOH or KOH at about 200° C. to 400° C. and preferably, about 325° C. to 375° C. With the second phase of the process, eliminating the cellulose and other organic and combustible components followed by washing away gypsum, vermiculite and other soluble components.

It is another object of the invention, to pursue a second phase of testing which may be employed on a separate previously unprocessed portion of the same sample as described herein.

It is another object of the present invention to permit such testing so as to determine quantitatively whether a vermiculite-containing material contains a predetermined threshold percentage of asbestos so as to require remedial action.

These and other objects of the invention will be more fully understood from the following description of the invention, on reference to the drawings appended hereto.

DESCRIPTION OF THE PREFERRED EMBODIMENTS

As employed herein, the term "asbestos" shall mean an amphibole or serpentine mineral in the asbestiform habit, whether or not recognized as "asbestos" by OSHA. These shall include, but are not limited to, the amphibole minerals winchite and richterite. Six naturally occurring silicate minerals, when found in certain fibrous forms, are referred to as "asbestos" by OSHA (29 CFR 1910.1001(b) and regulated as carcinogens. According of OSHA, "Asbestos includes chrysotile, Amosite, Crocidolite, tremolite asbestos, anthophyllite asbestos, actinolite asbestos, and any of these minerals that have been chemically treated and/or altered."

The minerals that can occur as "asbestos" (asbestiform) fall into two families: serpentine and amphibole. Serpentine and amphibole minerals occur in asbestiform and asbestiform habits. Minerals with a asbestifom morphology are not regulated as asbestos. As set forth in the '93 EPA Bulk Method, a population of asbesiform fibers is generally recognized by the following characteristics: (i) mean aspect ratios ranging from 20:1 to 100:1 or higher for fibers longer than 5 µm; (ii) thin fibrils, usually less than 0.5 µm in width, consisting of two or more of the following: parallel fibers occurring in bundles, fiber bundles displaying splayed ends, matted masses of individual fibers and/or fibers showing curvature. Id. Cite EPA R93. Asbestos is a commercial, not a mineralogical, term. Additionally as pointed out by the NY DOH, certain other amphiboles can form in an asbesiform habit and are found in association with vermiculite as naturally occurring asbestos, but are not regulated by OSHA.

The EPA defines "asbestos-containing material" as any material or product that contains more than one percent asbestos. Asbestos Hazard Emergency Response Act (AHERA), Fed. Reg., 52 (210), 41845 (1987); see also National Emission Standards for Hazardous Pollutants (NESHAP), Fed. Reg. 55 (224), 48405 (1990).

In performing the method under the present invention, if the vermiculite-containing materials are determined to have a quantity of asbestos greater than 1% by weight, the material will be deemed to be an asbestos contaminating material (ACM).

Figure 1:
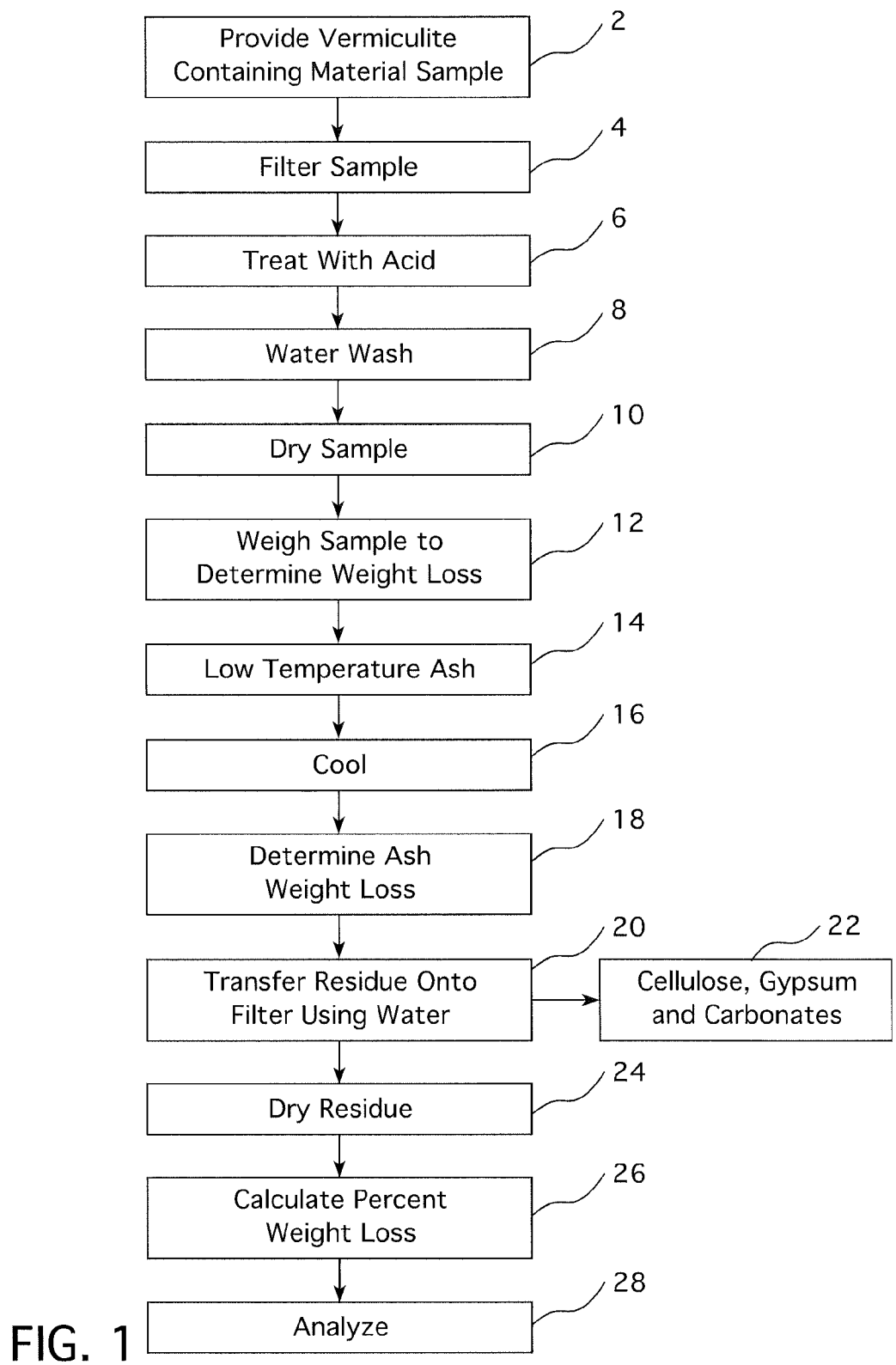
FIG. 1 is a flow diagram of a first method of the present invention.

In a level 1 portion of the process with reference to FIG. 1, a vermiculite-containing material sample 2 is provided in dried form. A representative sample will have been obtained by any suitable method such as, for example, cone and quartering or riffle splitting techniques in order to collect an appropriate sample 2 which is then reduced to a subsample having a size which preferably will weigh about 0.1 grams to 1.0 grams. The subsample is then placed in filtering apparatus 4 and a suitable acid 6 such as HCl having a concentration of about 0.1 N to 2 N and preferably about 0.5 N to 1.2 N is added in the amount of about 10 ml to 100 ml, preferably about 15 ml. When the sample has stopped effervescing, at least two liters of deionized water 8 are employed to wash the sample. The filter is then removed and placed in a drying oven at about 40° C. to 70° C. to dry the sample 10. The weight loss 12 during the process is then measured.

After that, the residue is introduced into a pre-weighed vessel having a suitable cover. Low temperature ashing 14 is preferably accomplished in a muffle furnace which starts at room temperature and then is heated for a minimum of two hours at about 450° C. to 550° C. The material is then allowed to cool 16 and the ash weight loss is determined 18. Subsequently, the residue is placed on a filter using deionized or distilled water 20, and cellulose, gypsum and carbonates will be separated 22 from the sample at this point. The residue is dried 24 at about 40° C. to 70° C. The percentage weight loss 26 can then be determined by weighing. The specimen is then analyzed as by polarized light microscopy to determine asbestos content. In addition to polarized light microscopy, this specimen can be analyzed by transmission electron microscopy, and scanning electron microscopy to determine asbestos content. The sample is analyzed to obtain a quantitative determination of the amount of asbestos in the specimen 26. Analysis may preferably be performed by employing the polarized light microscopy point count method.

Figure 2:
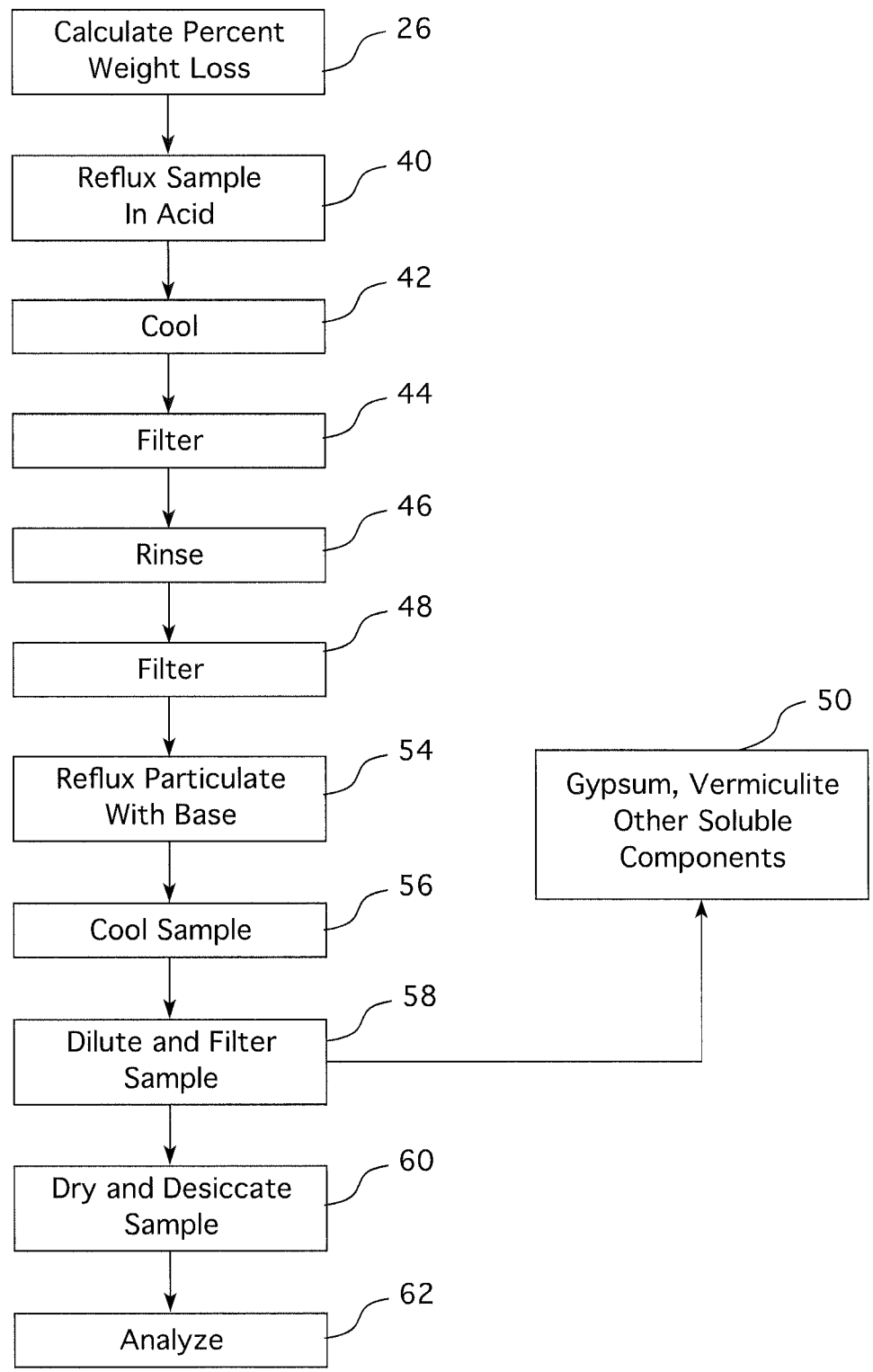
FIG. 2 is a flow diagram of a method which may be performed subsequent to and in combination with the method of FIG. 1.

The testing may be ended at that point or, if a more refined test is desired, additional testing may be performed on a second subsample of the original material or as shown in FIG. 2, on the residue from the first test (FIG. 1).

Referring to FIG. 2, there is shown a second test which may be employed to obtain additional analysis if desired. It may start with residue from the first test after the calculation of percent weight loss 26 (FIG. 1). The specimen is then refluxed in acid 40, selected from the group consisting of HCl, HBr, HCrO$_4$, HNO$_3$, citric acid and formic acid in a concentration below 1.2 N at a temperature of about 200° C. to 250° C. and preferably at the boiling point for about 1 to 1.5 hours and preferably about 0.5 to 2 hours, effecting by the acid refluxing a reduction in volume by washing away gypsum, vermiculite and other soluble components, cooled 42, filtered 43 and rinsed 46. This is followed by filtering 48 and separation of the gypsum, vermiculite and other soluble components 50. The particulate is then refluxed 54 with 4M NaOH at about 200° C. to 400° C. and preferably about 325° C. to 375° C. for a period of 2 to 4 hours. The sample is allowed to cool 56 and diluted and filtered 58 followed by drying and desiccating 60. Analyzing 62 is achieved through at least one procedure selected from the group consisting of polarized light microscopy, transmission electron microscopy, scanning electron microscopy and X-ray diffraction.

Where the first test (Level I) is the sole testing done on the subspecimen, the digestion step may be performed before the ashing or, if desired, the ashing may be performed before digesting. It is preferred, however, to perform the digesting before the ashing.

In an alternate embodiment of the invention, Level I testing is performed independently of Level II testing with the following examples providing a disclosure of a preferred approach to Level I sampling and the Level II sampling being performed on a separate subsample obtained from the same material as was tested in Level I. Unlike Level I wherein the digestion and ashing may be performed with either procedure coming first, it is preferred in Level II to perform the ashing first as the ashing dehydrates the vermiculite and facilitates enhanced digestion.

In order to provide additional insight into a preferred practice of the invention, examples will be considered.

EXAMPLE 1—Level I Testing

1. Digestion of gypsum and carbonate minerals
   A. Ensure that the samples are dry before subsampling.
   B. Use cone and quartering or riffle splitting techniques to collect a representative sample and subsample 0.1 g to 1.0 g.
   C. The subsample is placed into the filtering apparatus and 15 ml of HCl is added. When the sample has stopped effervescing, a minimum of 2 liters of deionized water is filtered through.
   D. The filter is then removed and placed in a drying oven at 60° C. to dry.
   E. Measure the weight loss using a balance
2. Sample Ashing
   A. Place the residue into a pre-weighed vessel with a lid.
   B. Ash in a muffle furnace stating at room temperature and then heated for a minimum of 2 hours at about 450° C. to 550° C. (450° C. to 550° C.).
   C. Cool and determine ash weight loss.
   D. Transfer the residue onto a filter using deionized or distilled water then dry residue at 60° C.
   E. Calculate percent weight loss by weighing.
3. Analyze by PLM Point Count Method.

EXAMPLE 2—Level II Testing

1. Sample Ashing
   A. Use cone and quartering or riffle splitting techniques collect a representative sample and subsample 0.1 g to 1.0 g.
   B. Place the subsample into a pre-weighed vessel with a lid.
   C. Ash in a muffle furnace stating at room temperature and then heated for a minimum of 2 hours at 480° C. (450° C. to 550° C.).
   D. Cool and determine ash weight loss.
   E. Transfer the residue onto a filter using deionized or distilled water then dry residue at 60° C.
   F. Calculate percent weight loss by weighing.
2. Sample Digestion
   A. Transfer the pre-weighed, ashed sample into a beaker and reflux in 100 mL of concentrated HCl at 250° C. for 1 hr.
   B. Allow samples to cool and filter through a 0.8 µm polycarbonate filter.
   C. Rinse thoroughly and completely filter.
   D. Transfer particulate back into the 250 mL beaker and reflux with 50 ml. of 4M NaOH 350° C. for 1 hour.
   E. Allow samples to cool and dilute up to 200 ml with DI water and filter onto a 0.2 µm polycarbonate filter.
   F. Dry samples and desiccate.
   G. Split filters for PLM, TEM, SEM, and XRD analysis.

It will be appreciated that the present invention provides an efficient reliable means for effecting quantitative determination of the amount of asbestos in vermiculite-containing materials. This is accomplished employing low acid levels with ashing being achieved at low temperatures. Depending upon the objectives, one may use only the first stage of testing and make the analysis or employ a second stage of testing to get additional analysis performed. The second stage among other things, provides for separation of the vermiculite. The second stage may either be performed on the residue of the first stage of testing or may be employed on a separately obtained subsample from the same material being tested.

Whereas particular embodiments of the invention have been described hereinbefore, for purposes of illustration, it will be evident to those skilled in the art that numerous variations of the details may be made without departing from the invention as defined in the appended claims.

What is claimed is:

1. A method for quantitative analysis of asbestos in a vermiculite-containing material comprising,
    providing a sample of said vermiculite-containing material,
    placing said vermiculite-containing material in a filtering apparatus,
    treating said sample with a material selected from the group consisting of water and an acid selected from the group consisting of HCl, HBr, $HCrO_4$, $H_2SO_4$, $HNO_3$, citric acid, acetic acid, and formic acid, in a concentration of about 0.1 N to 1.5 N,
    washing the sample with water,
    dry said washed sample,
    determine weight loss of said sample from residue of said drying,
    after determining said weight loss ash the residue of said sample at about 450° C. to 550° C. for about 1 to 3 hours,
    cool said sample,
    determine ash weight loss,
    employing water to transfer the sample residue to a filter,
    dry the residue,
    calculate percentage weight loss, and
    analyze the sample to determine the quantity of asbestos in said vermiculite-containing material, whereby cellulose, gypsum and carbonates have been removed from said sample prior to said analysis
    subsequent to said ashing and calculation of the sample percent weight loss performing additional processing of said sample by refluxing said ash sample in an acid selected from the group consisting of HCl, HBr, $HCrO_4$, $HNO_3$ citric acid, acetic acid, and formic acid at a temperature of about 200° C. to 250° C. for about 1 to 1.5 hours,
    allow the sample to cool, water wash and filter the same,
    reflux the sample with a base at about 200° C. to 400° C. for about 2 to 4 hours,
    effecting by said acid refluxing a reduction in volume by washing away gypsum, vermiculite and other soluble components,
    after said sample has cooled, dilute said sample with water and filter,
    dry the sample,
    weigh the sample, and
    analyze the sample.

2. The method of claim 1 including,
    effecting said analysis in said additional processing employing at least one process selected from the group consisting of polarized light microscopy, transmission electron microscopy, scanning electron microscopy and X-ray diffraction.

3. The method of claim 1 including,
    if said analysis of said sample indicates that the vermiculite-containing material contains at least 1% asbestos concluding that the vermiculite-containing material is an asbestos-containing material.

4. The method of claim 1 including,
    if said analysis of said sample indicates that the vermiculite-containing material contains at least 1% asbestos concluding that the vermiculite-containing material is an asbestos-containing material.

5. The method of claim 1 including,
    employing said acid in a concentration below 1.2 N.

6. The method of claim 1 including,
    in providing said sample reducing said vermiculite-containing material from bulk material to provide a portion in the form of released fiber material.

7. The method of claim 1 including,
    employing a sample having a weight of about 0.1 to 1.0 grams.

8. The method of claim 1 including,
    determining by said analysis whether amphibole asbestos is present by employing the polarized light microscopy.

9. The method of claim 1 employing,
    determining by said additional processing whether naturally occurring amphibole asbestos is present.

10. The method of claim 1 including,
    effecting by said method destruction of chrysotile present in said sample.

11. The method of claim 10 including,
    effecting by said method freeing of amphibole trapped in said vermiculite.

12. A method for quantitative analysis of asbestos in a vermiculite-containing material comprising,
    providing a sample of said vermiculite-containing material,
    ashing said sample at a temperature of about 450° C. to 550° C. to create an ashed residue,
    permitting the ashed residue to cool,
    determining the ash weight loss,
    calculating percent weight loss by weighing said ashed residue,
    refluxing the ashed residue with an acid selected from the group consisting of HCl, HBr, $HCrO_4$, $H_2SO_4$, $HNO_3$, citric acid, acetic acid and formic acid at a temperature of about 200° C. to about 250° C. for about 1 to 1.5 hours,
    allowing the sample to cool,
    water washing and filtering the same,
    refluxing the sample with a base at about 200° C. to 400° C. for about 2 to 4 hours,
    effecting by said acid refluxing a reduction in volume by washing away gypsum, vermiculite and other soluble components,
    after said sample is cooled, dilute said sample with water and filter,
    dry the sample,
    weigh the sample, and
    analyze the same.

13. The method of claim 12 including,
    effecting said analysis employing at least one process selected from the group consisting of polarized light microscopy, transmission electron microscopy, scanning electron microscopy and X-ray diffraction.

14. The method of claim 12 including,
    if said analysis of said sample indicates that the vermiculite-containing material contains at least 1% asbestos concluding that the vermiculite-containing material is an asbestos-containing material.

15. The method of claim 12 including,
    employing as said acid in a concentration below 1.2 N.

16. The method of claim 12 including,
in providing said sample reducing said vermiculite-containing material from bulk material to provide a portion in the form of released fiber material.

17. The method of claim 12 including,
employing a sample having a weight of about 0.1 to 1.0 grams.

18. The method of claim 12 including,
determining by said analysis amphibole asbestos is present by employing the polarized light microscopy.

19. The method of claim 12 employing,
determining whether naturally occurring amphibole asbestos is present.

20. The method of claim 12 including,
employing as said base a material selected from the group consisting of NaOH and KOH.

21. The method of claim 14 including,
effecting by said method destruction of chrysotile present in said sample.

22. The method of claim 12 including,
effecting by said method freeing of amphibole trapped in said vermiculite.

\* \* \* \* \*

UNITED STATES PATENT AND TRADEMARK OFFICE
CERTIFICATE OF CORRECTION

PATENT NO. : 9,291,611 B2
APPLICATION NO. : 13/918071
DATED : March 22, 2016
INVENTOR(S) : Richard J. Lee et al.

Page 1 of 1

It is certified that error appears in the above-identified patent and that said Letters Patent is hereby corrected as shown below:

In The Specification

Column 6, line 11, "1. Digestion of gypsum and carbonate minerals" should read
--*1. Digestion of gypsum and carbonate minerals*--.
Column 6, line 23, "2. Sample Ashing" should read --*2. Sample Ashing*--.
Column 6, line 36, "1. Sample Ashing" should read --*1. Sample Ashing*--.
Column 6, line 48, "2. Sample Digestion" should read --*2. Sample Digestion*--.

In The Claims

Column 9, line 9, Claim 18, "analysis amphibole" should read --analysis whether amphibole--.
Column 9, line 17, Claim 21, "claim 14" should read --claim 12--.
Column 9, line 20, Claim 22, "claim 12" should read --claim 21--.

Signed and Sealed this
Twenty-eighth Day of June, 2016

Michelle K. Lee
*Director of the United States Patent and Trademark Office*